United States Patent
Porchia et al.

(10) Patent No.: US 8,955,765 B2
(45) Date of Patent: Feb. 17, 2015

(54) DIFFUSION DEVICE WITH ODOR SENSOR

(75) Inventors: Jose Porchia, Greenfield, WI (US);
Hermann Neumann, Kenosha, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 578 days.

(21) Appl. No.: 12/229,115

(22) Filed: Aug. 20, 2008

(65) Prior Publication Data

US 2010/0044453 A1 Feb. 25, 2010

(51) Int. Cl.
*A61L 9/04* (2006.01)
*A61L 9/12* (2006.01)
*A01M 1/20* (2006.01)
*A61L 9/14* (2006.01)

(52) U.S. Cl.
CPC ............... *A61L 9/127* (2013.01); *A01M 1/205* (2013.01); *A61L 9/14* (2013.01); *A61L 2209/111* (2013.01)
USPC .............. 239/67; 239/44; 239/71; 239/102.2; 239/326; 222/52; 222/187

(58) Field of Classification Search
USPC ................. 239/71–74, 34–60, 67, 69, 102.1, 239/102.2, 326; 73/23.32–23.42; 222/57, 222/187
See application file for complete search history.

(56) References Cited

U.S. PATENT DOCUMENTS

| | | | |
|---|---|---|---|
| 4,031,171 A * | 6/1977 | Asao et al. ..................... 261/1 |
| 5,051,240 A | 9/1991 | Nakai et al. |
| 5,894,001 A | 4/1999 | Hitzler et al. |
| 6,085,576 A | 7/2000 | Sunshine et al. |
| 6,093,308 A | 7/2000 | Lewis et al. |
| 6,354,135 B1 | 3/2002 | McGee et al. |
| 6,467,332 B1 | 10/2002 | Bertschi et al. |
| 6,495,375 B2 | 12/2002 | Ledig |
| 6,511,852 B1 | 1/2003 | Ledig |
| 6,672,129 B1 | 1/2004 | Frederickson et al. |
| 6,708,550 B2 | 3/2004 | McGee et al. |
| 6,877,358 B2 | 4/2005 | Beckwith |
| 6,881,585 B1 * | 4/2005 | Potyrailo et al. .............. 436/151 |
| 7,849,851 B2 * | 12/2010 | Zierenberg et al. ...... 128/200.14 |
| 2005/0247305 A1 * | 11/2005 | Zierenberg et al. ...... 128/200.14 |
| 2006/0175426 A1 * | 8/2006 | Schramm et al. ................ 239/69 |
| 2010/0143186 A1 * | 6/2010 | Belmonte et al. ................. 422/3 |
| 2012/0230864 A1 | 9/2012 | An et al. |
| 2012/0237404 A1 | 9/2012 | Woolley |

FOREIGN PATENT DOCUMENTS

| | | |
|---|---|---|
| EP | 2 111 875 | 10/2009 |
| GB | 2233230 A | 1/1991 |
| JP | 03-007822 | 1/1991 |
| JP | 4-288164 | 10/1992 |
| JP | 6-142173 | 5/1994 |
| JP | H7-2822 | 1/1995 |

(Continued)

OTHER PUBLICATIONS

International Search Report and Written Opinion dated Feb. 2, 2010 Appl. No. PCT/US2009/004742.

*Primary Examiner* — Jason Boeckmann

(57) ABSTRACT

An apparatus for treating an airspace with a volatile substance includes means for detecting the presence of a specific component in a volatile substance and means for controlling a volatile substance dispenser to dispense the volatile substance only if the volatile substance contains the specific component.

4 Claims, 6 Drawing Sheets

(56) References Cited

FOREIGN PATENT DOCUMENTS

| | | |
|---|---|---|
| JP | 2002-200157 | 7/2002 |
| WO | 0232470 A | 4/2002 |
| WO | 03011348 A | 2/2003 |
| WO | 03071686 A | 8/2003 |
| WO | 2004002542 | 1/2004 |
| WO | 2005018690 | 3/2005 |
| WO | WO 2005/018690 | 3/2005 |
| WO | 2006087515 | 8/2006 |
| WO | 2006095131 | 9/2006 |
| WO | 2007107750 | 9/2007 |
| WO | 2007107755 | 9/2007 |
| WO | 2007107769 | 9/2007 |
| WO | 2007148054 | 12/2007 |
| WO | 2008056131 | 5/2008 |
| WO | 2008059210 | 5/2008 |
| WO | 2008068486 | 6/2008 |
| WO | 2008149064 | 12/2008 |
| WO | 2008149065 | 12/2008 |
| WO | 2008149066 | 12/2008 |
| WO | 2009060212 | 5/2009 |
| WO | 2010122279 | 10/2010 |

* cited by examiner

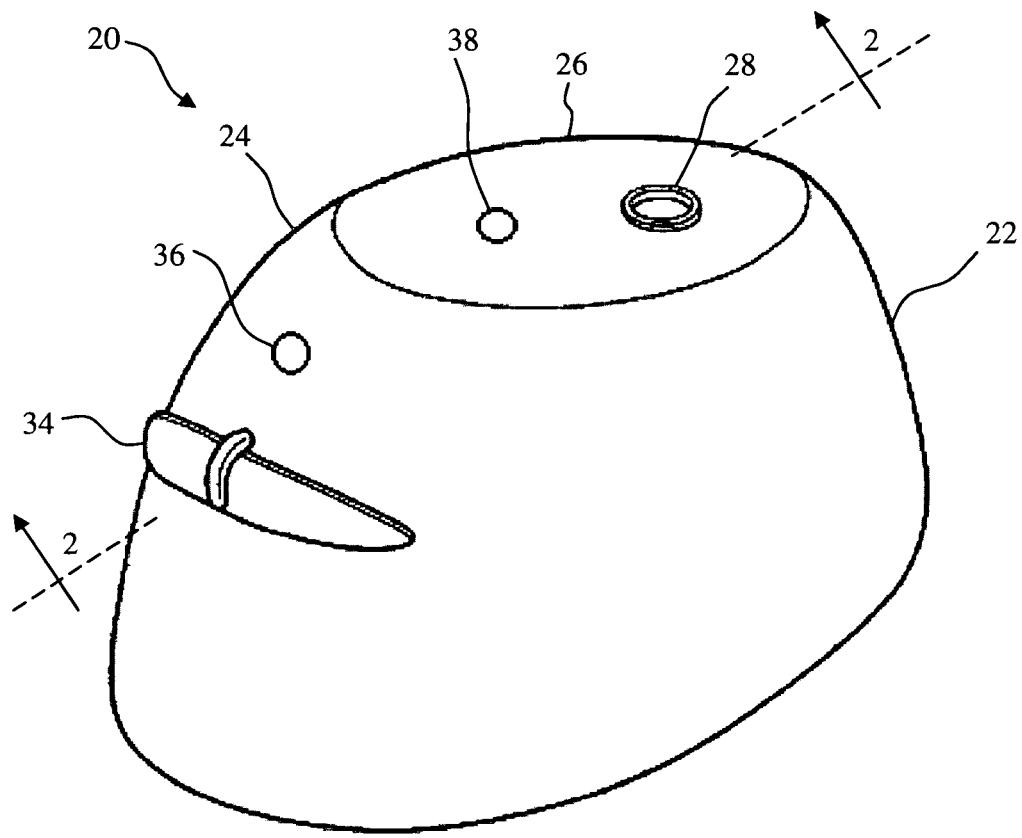
FIG. 1
FIG. 3
FIG. 4

DIFFUSION DEVICE WITH ODOR SENSOR

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to diffusion devices and, more particularly, to diffusion devices that include an odor sensor.

2. Description of the Background of the Invention

Diffusion devices or dispensers are used to disperse volatile materials such as perfumes, deodorizers, insecticides, insect repellants, and the like. Many such devices are passive diffusion devices that require only ambient air flow to disperse the volatile material. Other devices are active diffusion devices that may include a heating element for heating a volatile material to promote vaporization thereof. Other active diffusion devices employ a fan to generate air flow to direct the volatile material out of the diffusion device and into the surrounding environment. Still other diffusion devices utilize an ultrasonic transducer to break up a liquid volatile material into droplets that are ejected from the device.

In light of the wide variety of diffusion devices, a need has developed to control the amount of volatile material that is dispensed into the environment. For example, a passive device will merely disperse the volatile material in an uncontrolled manner even during periods when the benefits of the volatile material are not being experienced, e.g., if a perfume is being dispersed into an empty room or into a room that already has a sufficient level of the perfume. Some of the diffusion devices mentioned above address this issue through the use of odor sensors to sense malodors, e.g., sulfur or cigarette smoke, wherein the diffusion devices are controlled to disperse a volatile material in response to the detection of such malodors. However, typical diffusion devices with odor sensors are complex because such sensors are designed to sense a wide range of chemicals that comprise a multitude of malodors, e.g., hydrogen sulfide, methanethiol, dimethyl sulfide, ammonia, nitrogen dioxide, carbon monoxide, etc. The complexity of such odor sensors affects the size, cost, and implementation of such diffusion devices. Further, many of these known diffusion devices do not employ a mechanism to prevent the dispensing of an inappropriate volatile material that has been inadvertently placed into the diffusion device. Utilization of an inappropriate volatile material may harm the diffusion device because of an incompatibility with a reservoir containing the material or may result in user dissatisfaction by having an incorrect volatile material dispensed into an airspace. Therefore, a need exists for an improvement over prior art diffusion devices that employ odor sensors.

SUMMARY OF THE INVENTION

According to one embodiment, an apparatus for treating an airspace with a volatile substance includes means for detecting the presence of a specific component in a volatile substance and means for controlling a volatile substance dispenser to dispense the volatile substance only if the volatile substance contains the specific component.

According to another embodiment, an apparatus for treating an airspace with a volatile substance includes means for detecting a quantity of a specific component of a volatile substance in an airspace and means for controlling a volatile substance dispenser to dispense the volatile substance in response to the detected quantity of the specific component falling below a specified level.

According to yet another embodiment, a method for treating an airspace with a volatile substance includes the steps of providing a reservoir containing a volatile substance with a specific component and detecting a quantity of the specific component in an airspace. Further, the method includes the step of dispensing the volatile substance from the reservoir into the airspace in response to the detected quantity of the specific component being below a specified level.

Other aspects and advantages of the present invention will become apparent upon consideration of the following detailed description.

BRIEF DESCRIPTION OF THE DRAWINGS

FIG. 1 is an isometric view of a first embodiment of a diffusion device;

FIG. 3 is an isometric view of an ultrasonic actuator of the diffusion device of FIG. 2;

FIG. 4 is an odor sensor of the diffusion device of FIG. 2;

DETAILED DESCRIPTION OF THE DRAWINGS

Figure 2:
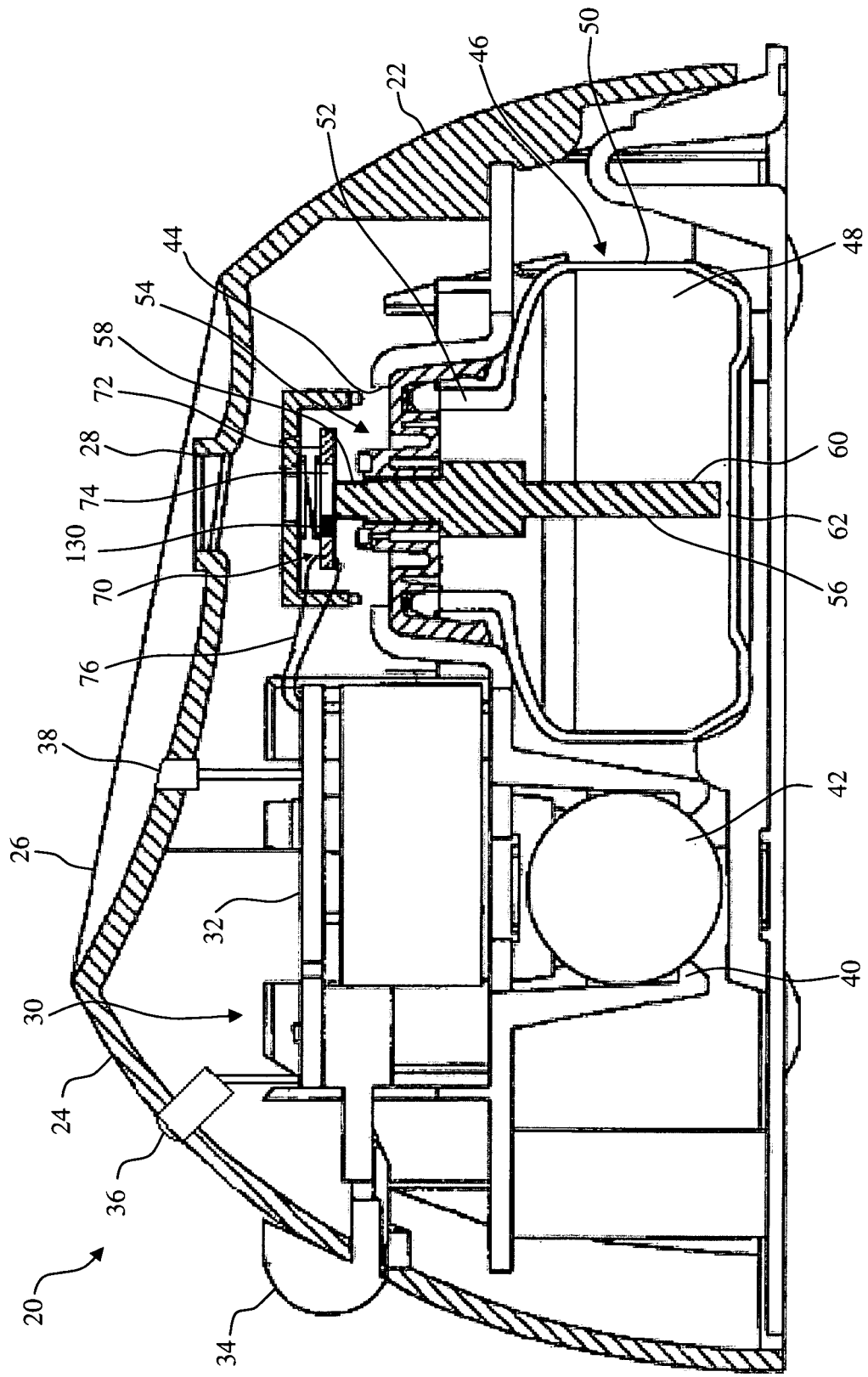
FIG. 2 is a cross sectional view of the diffusion device of FIG. 1 taken generally along lines 2-2.

FIGS. 1 and 2 depict a diffusion device 20 that includes a housing 22. The housing 22 has a top portion 24 with a concave depression 26 disposed therein. An aperture 28 extends through the top portion 24 within the concave depression 26. The aperture 28 is appropriately sized to allow emission of a fluid, such as an atomized liquid, therethrough.

Referring to FIG. 2, the diffusion device 20 includes a support chassis 30 disposed within the housing 22. The chassis 30 supports a printed circuit board (PCB) 32 and control circuitry for the diffusion device 20. The PCB 32 is responsive to a movable selector switch 34, which is used to select an operating mode and/or a rate at which the device disperses the atomized liquid. A light emitting diode ("LED") 36 is coupled to the PCB 32 and is used to provide an indication of an operational state of the diffusion device 20. An odor sensor 38 is also coupled to the PCB 32, the operation of which will be described in greater detail hereinafter. In the present embodiment, the odor sensor 38 is disposed within the concave depression 26. In other embodiments the odor sensor 38 can be disposed anywhere on the diffusion device 20 or can even be separate from the diffusion device 20.

A battery mount 40 for a battery 42 is also attached to the chassis 30. In the present embodiment, the battery mount 40 is adapted to hold a single 1.5 volt AA battery to supply power to the diffusion device 20. However, if desired, the single battery may be replaced by any number of batteries or other power sources.

The chassis 30 further includes an opening 44, which is adapted to receive a replaceable fluid reservoir 46. The fluid reservoir 46 includes a volatile material 48 in liquid form therein, wherein the volatile material 48 can be a fragrance, a disinfectant, a sanitizer, an air purifier, an aromatherapy scent, an antiseptic, an odor eliminator, an air-freshener, a deodorizer, an insecticide, an insect repellant, an insect attractant, or any other volatile material(s) that are usefully dispersed into an airspace or ambient environment. In the present embodiment, the fluid reservoir 46 has a generally cylindrical body 50 with a neck 52. A combination plug and wick holder 54 is affixed to the neck 52. The plug and wick holder 54 holds a wick 56 that is disposed within the reservoir 46 and is in contact with the volatile material 48. An upper end 58 of the wick 56 extends beyond the neck 52 and a lower end 60 of the wick is disposed within the reservoir 46 toward a bottom surface 62 thereof. The wick 56 transfers volatile material by capillary action from within the reservoir 46 to the upper end 58 of the wick 56. The fluid reservoir 46 can be inserted into the chassis 30 and secured by any known method, e.g., by a threaded engagement, a snap-fit engagement, an interference fit, a bayonet connection, etc., as would be apparent to one of ordinary skill in the art.

Referring to FIGS. 2 and 3, the diffusion device 20 includes an ultrasonic actuator such as a piezoelectric actuator 70. The piezoelectric actuator 70 has a piezoelectric element 72 and an orifice plate 74, e.g., the piezoelectric actuator 70 of the present embodiment may comprise any of the piezoelectric actuators described in Helf et al. U.S. Pat. No. 6,896,193, which is incorporated by reference herein in its entirety, or the piezoelectric actuator found in the WISP® brand Flameless Candle sold by S.C. Johnson and Son, Inc., of Racine, Wis. Alternatively, other known ultrasonic actuators may similarly be used in other embodiments. The piezoelectric actuator 70 is mounted within the body 22 of the diffusion device 20 above the opening 44 and in alignment with the wick 56 of the fluid reservoir 46, which extends through the opening 44. With reference to FIG. 3, it is shown that the orifice plate 74 is generally cylindrical in shape with an outer circumferential portion of the orifice plate in contact with the piezoelectric element 72. The orifice plate 74 includes perforations or holes (not seen due to the scale of the drawings) of nominally equal diameter that extend therethrough.

The piezoelectric element 72 is connected by wires 76 to the PCB 32. The wires 76 supply an alternating electrical voltage produced by the PCB 32 to opposite sides of the piezoelectric element 72. A diameter of the piezoelectric element 72 alternately increases and decreases in size when alternating electrical voltages are applied to the element 72, thereby causing the orifice plate 74 to vibrate up and down due to the contact of the element 72 with the orifice plate 74. The orifice plate 74 is in fluid communication with the volatile material 48 supplied by the wick 56, wherein the vibration of the orifice plate 74 causes the volatile material 48 to be driven through the perforations or holes in the orifice plate 74. Subsequently, the volatile material 48 is emitted upwardly in the form of aerosolized particles, which pass through the aperture 28 of the housing 22 and into the surrounding environment or airspace. The PCB 32 can be adapted to energize the piezoelectric element 72 in the above manner for any duration to disperse any amount of volatile material. For example, the PCB 32 can energize the piezoelectric element 72 to disperse a relatively small amount of the volatile material during a short duration, e.g., 500 milliseconds, or a larger amount during a longer duration, e.g., 10 seconds, as would be apparent to one of ordinary skill in the art.

In some embodiments the PCB 32 includes a microcontroller and/or an application specific integrated circuit. In one embodiment, the PCB 32 is similar to the PCB in the WISP® brand Flameless Candle identified above. In another embodiment, the PCB 32 is similar to the PCB described in Blandino et al. U.S. application Ser. Nos. 11/464,419 or 11/639,904, which are both incorporated by reference herein in their entireties.

Referring to FIG. 4, one example of a simple odor sensor 38 is shown, which is a chemical sensor that includes first and second electrical leads 80, 82, respectively, separated by a conducting polymer 84. The impedance of the odor sensor 38 varies as a function of exposure to a specific chemical component. In the present embodiment, the presence of the specific chemical component is sensed by applying a constant voltage differential across the first and second electrical leads 80, 82 and analyzing the resulting current. Further, the concentration or quantity of the chemical component in a sample is detected by analyzing the magnitude of the change in the impedance. In one embodiment, the odor sensor 38 is similar or identical to the sensor disclosed in Lewis U.S. Pat. No. 6,093,308, which is herein incorporated by reference in its entirety.

In the present embodiment, the odor sensor 38 is tuned to a specific chemical, i.e., made more sensitive or responsive to a specific chemical component, by varying the composition of the conducting polymer 84. Modifying the composition of a conducting polymer layer to accomplish such a tuning is known to those skilled in the art, e.g., Lewis U.S. Pat. No. 6,093,308 describes such a manufacturing process. The tuned odor sensor 38 is used to detect the presence and quantity of a specific chemical component in the volatile material 48 emitted by the device 20. The specific chemical component may be a neutral or active component in the volatile material 48. In a preferred embodiment, the specific chemical component is a neutral carrier or solvent in the volatile material 48. Further, the neutral carrier or solvent may be similarly placed in other volatile materials so that a plurality of different fragrances can include the same neutral component. In another embodiment, the ratio of the specific chemical component to other components comprising the volatile material 48 is known. It is also intended that the ratios of components may be varied among different volatile materials as would be apparent to one of skill in the art. In yet another embodiment, the specific chemical component is distributed homogenously throughout the volatile material 48 so that an accurate determination of the concentration of the volatile material 48 can be obtained throughout the life thereof as it is depleted.

Figure 5:
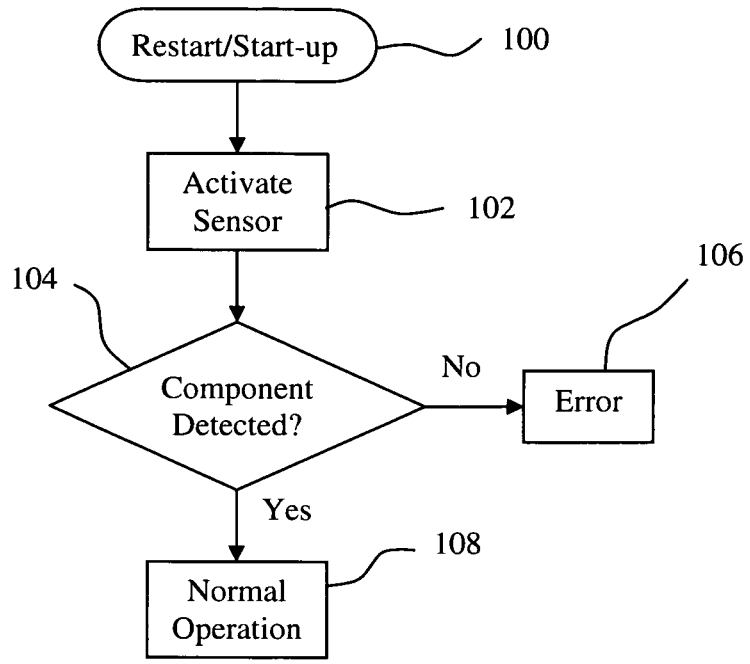
FIG. 5 is a flowchart that illustrates programming for a pre-operative sequence that may be executed by the diffusion device of FIG. 1.

Turning to FIG. 5, one embodiment of a pre-operative program or sequence performed by the PCB 32 to control the diffusion device 20 is shown, which initiates at a reset/start-up block 100. The initiation sequence at the block 100 is caused by turning the device 20 on, i.e., a start-up of the device 20, or by inserting and/or replacing the fluid reservoir 46 into the housing 22 when the device 20 is powered, i.e., a restart of the device 20. In one embodiment, the device 20 includes another sensor (not shown) that detects the insertion and/or removal of the fluid reservoir 46. After the block 100, control passes to a block 102 and a second odor sensor 103

(see FIGS. 2 and 3), which is a chemical sensor that is described with greater particularity below, is activated to analyze a sample of the volatile material 48. Next, a decision block 104 determines whether a specific chemical component has been detected by the second odor sensor 103. If the specific chemical component is not detected, then control passes to a block 106 and the PCB 32 will signal an error and not initiate the normal operation of the diffusion device 20. The error signaled by the block 106 may include a visual or audible signal, e.g., a flashing LED or a beeping sound, or any other signal or cue that would be apparent to one of ordinary skill in the art. If the specific chemical component is detected at the decision block 104, then the PCB 32 will enter a normal operation mode or sequence depicted at a block 108, which may include the periodic dispersal of the volatile material 48 in response to a timer and/or sensor, as will be described in greater detail hereinafter.

The pre-operative program of the present embodiment is characterized, in part, by a lock-and-key start-up sequence to ensure that an inappropriate fluid reservoir 46 has not been inserted into the housing 22. The second odor sensor 103 is adapted to detect a concentration of the specific chemical component adjacent the piezoelectric actuator 70. In the present embodiment, the second odor sensor 103 is positioned on the piezoelectric actuator 70 proximate the orifice plate 74 so that the sensor 103 is in fluid communication with the volatile material 48 supplied to the orifice plate 74 via the wick 56. The second odor sensor 103 analyzes the volatile material 48 to detect the presence of a specific chemical component and sends a signal to the PCB 32, which will energize the piezoelectric actuator 70 only if the specific chemical component is detected. As noted above, the error condition at the block 106 will be triggered if the second odor sensor 103 detects an incompatible volatile material 48. An incompatible volatile material 48 is found when the specific chemical component is not found in the volatile material 48 and/or the concentration of the specific chemical component is too low, which may indicate an empty fluid reservoir 46.

In a different embodiment of the lock-and-key mechanism, the first odor sensor 38 is used to detect the specific chemical component in the volatile material 48 during the pre-operative state. In the present embodiment, the PCB 32 energizes the piezoelectric actuator 70 to disperse the volatile material 48 during a startup operation (not shown) and the first odor sensor 38 analyzes the dispersed volatile material 48 for the specific chemical component. If the component is detected the PCB 32 transfers control of the diffusion device 20 to block 108 to initiate the normal operation mode. However, if the specific chemical component is not detected the PCB 32 will transfer control to block 106 and signal an error and not initiate the normal operation of the diffusion device 20. In this embodiment, the first odor sensor 38 performs a similar function as the second odor sensor 103, which can be omitted from the diffusion device 20 or retained and used in conjunction with the first odor sensor 38.

Figure 6:
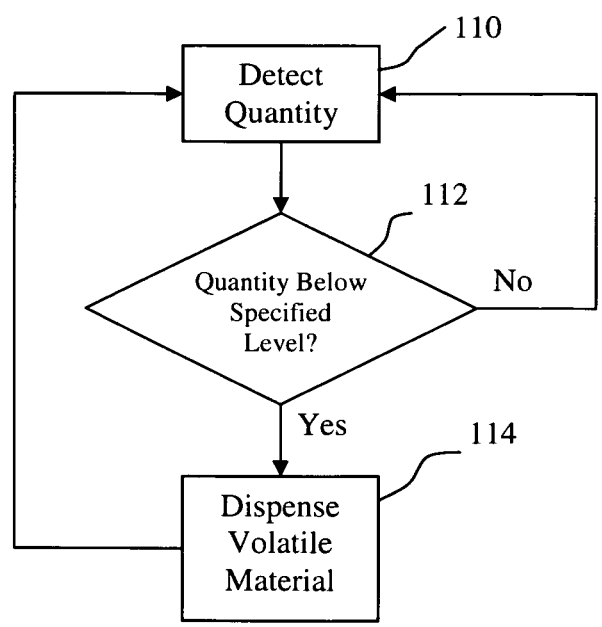
FIG. 6 is a flowchart that illustrates programming for a normal operational sequence that may be executed by the diffusion device of FIG. 1.

One embodiment of the normal operational mode programming of the diffusion device 20 is illustrated in FIG. 6. The normal operational mode is characterized, in part, by the emission of the volatile material 48 when a level or concentration thereof in an airspace or an environment is below a predetermined level. Specifically, during the normal operational mode the odor sensor 38 is periodically activated at a block 110 to detect a quantity of the specific chemical component in a small sample of an airspace or environment, e.g., a room in a house. Thereafter, the PCB 32 estimates a corresponding level or concentration of the volatile material 48 in the room. The correspondence between the quantity of the specific chemical component and the concentration of the volatile material 48 is determined using known methods, such as quantitative and/or qualitative analyses performed at a testing facility. In one example, a quantitative analysis is performed by dispersing a known quantity of the volatile material 48 into a room and using one or more of the odor sensors 38 to analyze the sensed quantity of the specific chemical component and the volatile material in samples taken throughout the room. In another example, a qualitative analysis is performed by dispersing a known quantity of the volatile material 48 into a room and using one or more of the odor sensors 38 to analyze the sensed quantity of the specific chemical component in the room while a person in the room indicates a user sensed level of the volatile material 48 in the room. Further, other data can be collected and/or tests performed to obtain a more precise correspondence between the specific chemical component and the concentration of the volatile material 48, as would be apparent to those having skill in the art, e.g., measuring the temperature and humidity, using different room sizes, generating airflows in the rooms, etc.

Upon the determination by the PCB 32 of the corresponding level or concentration of the volatile material 48 in the room, a decision block 112 determines whether the detected level or concentration is below a specified level. As discussed above, the quantity of the specific chemical component can be used to determine the level or concentration of the volatile material 48 in an environment such as a room. If the detected quantity is above the specified level, then control loops back to the block 110 and the odor sensor 38 continues to monitor the quantity of the specific chemical component in the airspace. If the detected quantity and the corresponding level of the volatile material 48 in the airspace is below the specified level, control passes to a block 114 and the volatile material 48 is dispensed. After the volatile material 48 is dispensed, control loops back to the block 110 and the odor sensor 38 continues to analyze the airspace for the level or concentration of the volatile material 48.

In yet another embodiment, after the block 114, control passes back to the block 104 of FIG. 5 to detect a threshold quantity of the specific chemical component before control passes back to the normal operational mode of the block 108. In this embodiment, if the concentration of the specific chemical component is too low, then an error or warning is signaled as described above to indicate that the fluid reservoir 46 is empty and should be replaced with a new fluid reservoir. In this manner, the programming of FIG. 6 is modified to avoid the repeated execution of the loop of the blocks 110, 112, and 114 when the fluid reservoir 46 has become depleted.

Figure 7:
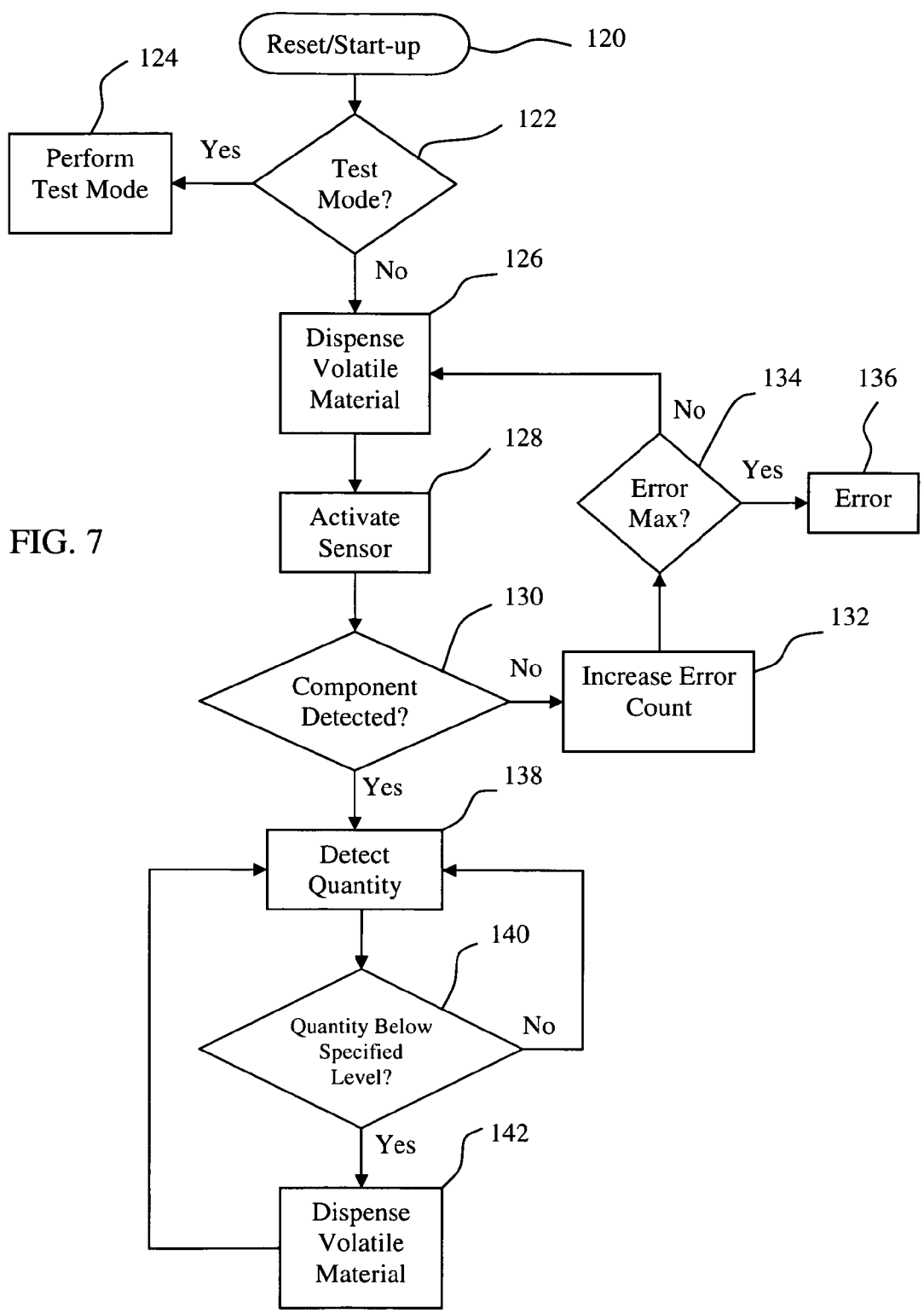
FIG. 7 is a flowchart that illustrates a different operational program that may be executed by the diffusion device of FIG. 1.

FIG. 7 illustrates yet another program that may be implemented by the PCB 32 to control the operation of the diffusion device 20, which initiates at a reset/start-up block 120. The reset/start-up block 120 is similar to the block 100 of FIG. 5. Thereafter, control passes to a decision block 122, which determines whether a test mode is to be performed. If the test mode is to be performed, then the test mode is performed at a block 124. In one embodiment, the test mode is performed at a manufacturing facility to ensure the proper operation of the diffusion device 20 before a consumer uses the diffusion device 20. For example, the test mode can include a test of the odor sensor(s) 38, 103 to ensure that a detected quantity of a specific chemical component of a volatile material 48 in a certain volume of airspace corresponds to an actual level or concentration of the volatile material 48. Other tests can also be performed as would be apparent to one of ordinary skill in the art. If a test mode is not performed, control passes to a block 126 and the volatile material 48 is dispensed into the airspace. Thereafter, control passes to a block 128 that activates the odor sensor 38.

In the present embodiment, the block 128 activates the odor sensor 38 to analyze the airspace in which the volatile material 48 was dispensed at the block 126. A decision block 130 determines whether a specific chemical component was detected in the airspace and, thus, whether the volatile material 48 contains the specific chemical component. If the specific chemical component is not detected, then control passes to an error loop that includes blocks 132, 134, and 136. The error loop analyzes one or more samples of the airspace before control determines that the volatile material 48 does not include the specific chemical component. More specifically, the block 132 increases an error count, which corresponds to the number of samples that have been analyzed. Control then passes to the block 134, which determines whether the error count (number of samples analyzed) has reached a maximum number of samples, e.g., four. If the error count has reached the maximum, then control passes to the error block 136. In one embodiment, the error block 136 prevents further dispensing of the volatile material 48 until the PCB is reset (block 120) and further flashes an LED to provide a visual cue to a user of the error. If the error count has not reached the maximum, then control passes back to the block 126 and another sample of the volatile material 48 is dispensed.

Referring again to the block 130, if the specific chemical component is detected in the airspace, then control passes to a block 138, which detects a quantity of the specific component in the airspace. After the quantity is detected, control passes to a decision block 140 and the quantity of the specific component in the airspace is compared to a specified level or range. In the present embodiment, the specified level or range can be adjusted by a user, e.g., through use of the selector switch 34. If the quantity is above the specified level or range, then control loops back to the block 138 and the odor sensor 38 continues to analyze the airspace. If the quantity is below the specified level or range then control passes to a block 142 and the volatile material 48 is dispensed. Following the block 142, control passes back to the block 138.

In another embodiment, the block 138 first detects a threshold quantity of the specific chemical component before control passes to the block 140 to determine whether the quantity is below a specified level. If the quantity of the chemical component is below the threshold quantity, then control passes to the block 136 and an error is signaled. Otherwise, control proceeds to the decision block 140. In this manner, the program of FIG. 7 determines when the fluid reservoir 46 is empty and signals an error instead of repeatedly executing the loop of the blocks 138, 140, and 142.

Figure 8:
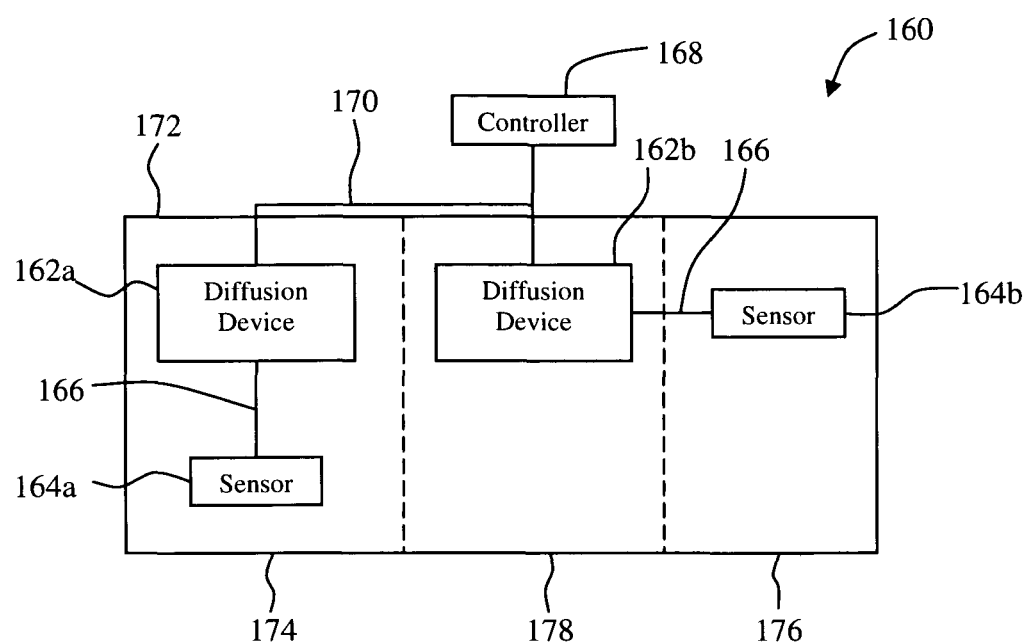
FIG. 8 is a block diagram that illustrates a system that incorporates first and second diffusion devices and first and second sensors.

FIG. 8 illustrates a system 160 that includes diffusion devices 162a and 162b that are similar to the diffusion device 20 of FIG. 1, but which are in communication with sensors 164a, 164b, respectively, that are remote or separate from the diffusion devices 162. The diffusion devices 162a, 162b communicate with the sensors 164a, 164b through communication lines 166, wherein the communication lines 166 may be a wired or wireless connection. A controller 168 communicates with the diffusion devices 162a, 162b via a similar wired or wireless communication line 170. In the present embodiment, the diffusion devices 162a, 162b are distributed throughout a building 172 that includes first and second rooms 174, 176, respectively, and an HVAC system 178. Specifically, the diffusion device 162a is positioned in the first room 174 remotely from the sensor 164a, e.g., the diffusion device 162a and the sensor 164a may be positioned at opposite ends of the room 174. Further, the diffusion device 162b is positioned in the HVAC system 178 and the sensor 164b is placed in the second room 176 remotely from the diffusion device 162b. The sensors 164a, 164b are operated to analyze the airspace in the first and second rooms 174, 176, respectively, for a specific chemical component or odor in a volatile material dispersed by the diffusion devices 162a, 162b. As described above, the detection of a specific chemical component can be used to estimate a level of the volatile material in the airspace. In the present embodiment, the controller 168 controls the diffusion devices 162a, 162b to disperse the volatile material therefrom in response to signals from the remote sensors 164a, 164b that the volatile material level is low in the first and second rooms 174, 176, respectively. Various modifications can be made to the embodiment described in FIG. 8 as would be apparent to one of skill in the art, e.g., additional rooms with diffusion devices and/or sensors may be provided, multiple sensors may be in communication with one or more diffusion devices, multiple diffusion devices may be in communication with one or more sensors, etc.

Figure 9:
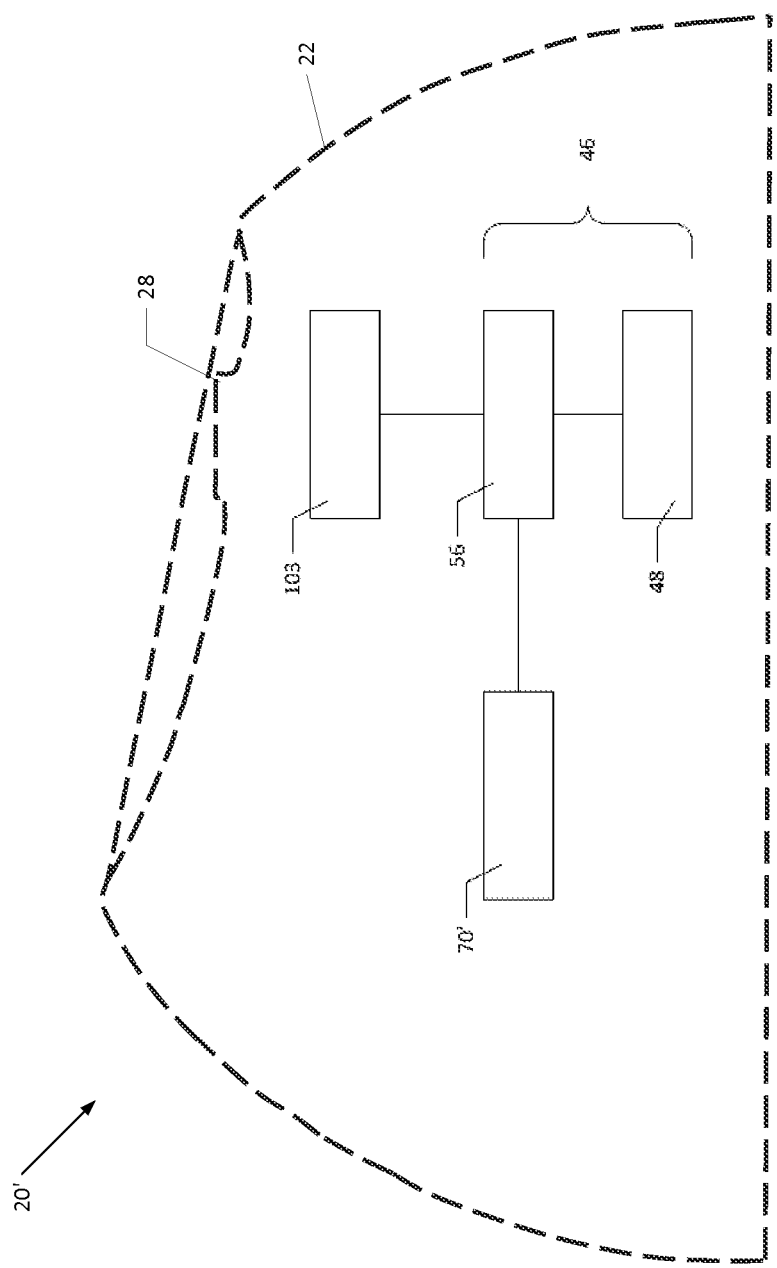
FIG. 9 is a schematic representation of another diffusion device.

In other embodiments, the means for emitting the volatile material 48 may be modified or completely altered within the diffusion device 20'. For example, the piezoelectric actuator 70 may be modified in light of other known piezoelectric actuators or replaced and/or supplemented by one or more of a heater, a fan, a valving mechanism, and a mechanical drive mechanism 70' for dispensing the volatile material 48 in response to a signal generated by one or more of a timer, a sensor, and a manual actuator (see FIG. 9).

Further, the volatile material 48 may be retained by a carrier that is a fluid, a gel, or a solid, and may be contained in any type of reservoir, e.g., within a bottle, in a compartment covered by a permeable membrane, in an aerosol container, etc. In one alternative embodiment, a diffusion device for dispensing a scented oil, such as the one disclosed in Pedrotti et al. U.S. Pat. No. 6,862,403, which is herein incorporated by reference in its entirety, may be modified with any of the odor sensors and/or methodologies described herein. Similarly, in other embodiments, diffusion devices for emitting volatile materials, such as the ones disclosed in Adams et al. U.S. Pat. No. 6,938,883, Carpenter et al. U.S. Publication No. 2007/0199952, Helf et al. U.S. Publication No. 2007/0237498, Beland et al. U.S. patent application Ser. No. 11/801,554, and Helf et al. U.S. patent application Ser. No. 11/893,532, which are herein incorporated by reference in their entireties, are modified to include any of the odor sensors and/or methodologies described herein.

In yet other embodiments, the diffusion device 20 can be adapted to compensate for user adaptation or habituation to the volatile material 48. In one embodiment, the PCB 32 includes programming that energizes the piezoelectric element 72 for different durations to vary the quantity of volatile material 48 dispersed. For example, the PCB 32 can include programming to dispense a high level of volatile material for one hour followed by a lower, yet still noticeable, level of volatile material for twenty minutes. In another embodiment, the operation of a fan or a heater can be varied in duration and/or intensity to vary the quantity of volatile material 48 dispersed or to vary the diffusion rate of the dispersed volatile material 48. In a further embodiment, different volatile materials 48 can be dispersed in varying sequences to compensate for user habituation. In yet another embodiment, the diffusion device 20 can be manually activated to disperse the volatile material 48 if desired by a user. Other methods and techniques to compensate for user habituation that would be apparent to one of ordinary skill in the art can be implemented in accordance with the present disclosure.

Further, other contemplated embodiments have additional sensors, e.g., a light sensor or heat sensor. In yet other embodiments, the diffusion device may include an array of odor or chemical sensors to detect multiple specific components and/or to more precisely detect a specific component. Further, other sensors that may be used include electrical leads separated by alternating conductive and nonconductive materials, such as those disclosed in Lewis U.S. Pat. No. 6,093,308. Still further, other sensors known to those of skill in the art, such as metal oxide sensors, micro-electromechanical sensors, surface acoustic wave sensors, quartz microbalance sensors, optical sensors, chemically reactive dye sensors, inkjet printed thin film sensors, biomimetric sensors, and the like, can be used with the presently described diffusion devices. More specifically, a non-exclusive and non-limiting lists of sensors that can be adapted for use in accordance with the present disclosure includes the Prometheus odor and VOC analyzer sold by Alpha M.O.S. of Hanover, Maryland, the Bloodhound™ ST214 sold by Scensive Technologies Limited of Normanton, West Yorkshire, United Kingdom, the Ball SAW Sensor developed by Toppan Printing Co., Ltd. of Tokyo, Japan, the LibraNOSE sold by Technobiochip of Pozzuoli, Naples, Italy, and the IPD-1000 particle detector sold by BioVigilant Systems, Inc. of Tucson, Ariz.

Other embodiments comprising various combinations of the individual features of each of the foregoing described embodiments are specifically included herein.

INDUSTRIAL APPLICABILITY

The diffusion devices described herein advantageously utilize an odor sensor to detect a specific chemical component in a volatile material to be dispensed. The detection of the specific chemical component can be used to identify a compatible volatile material and to control a diffusion device accordingly. Further, the quantity of the specific chemical component in the environment can be analyzed to provide an estimate of the level of a volatile material in the airspace and to control a diffusion device accordingly. Further, the design of the odor sensor and the overall diffusion device can be simplified because the odor sensor is configured to detect a specific chemical component instead of a wide range of components.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. An apparatus for treating an airspace with a volatile substance, comprising:
   a receptacle including a wick within the receptacle;
   a chemical sensor in fluid communication with the wick for detecting the presence of a specific component in a volatile substance disposed within the receptacle, the chemical sensor disposed outside of the receptacle; and
   means for controlling a volatile substance dispenser to dispense the volatile substance only if the volatile substance contains the specific component.

2. The apparatus of claim 1, wherein the apparatus includes a piezoelectric element and an orifice plate that are configured to dispense the volatile substance, and wherein the wick is adapted to deliver the volatile substance to the orifice plate.

3. The apparatus of claim 1, wherein the apparatus includes at least one of a heater, a fan, a valving mechanism, and a mechanical drive mechanism.

4. The apparatus of claim 1, further comprising means for signaling an error if the volatile substance does not include the specific component or if a receptacle for the volatile substance is depleted and should be replaced.

\* \* \* \* \*